United States Patent [19]

Omura et al.

[11] Patent Number: 4,493,845
[45] Date of Patent: Jan. 15, 1985

[54] ANTIBIOTIC AM-3603

[75] Inventors: Satoshi Omura, Tokyo; Yoshitake Tanaka, Machida; Yuzuru Iwai, Narita; Yoko Takahashi, Tokyo; Akira Nakagawa, Fuchu, all of Japan

[73] Assignee: Kitasato Kenkyusho, Tokyo, Japan

[21] Appl. No.: 434,818

[22] Filed: Oct. 18, 1982

Related U.S. Application Data

[63] Continuation-in-part of Ser. No. 298,695, Sep. 2, 1981, abandoned.

[30] Foreign Application Priority Data

Sep. 5, 1980 [JP] Japan .................................. 55-123283

[51] Int. Cl.³ .......................................... C07D 491/08
[52] U.S. Cl. ..................................... 424/279; 549/267
[58] Field of Search ......................... 549/267; 424/279

[56] References Cited

PUBLICATIONS

Aizawa et al., The Jour. of Antibiotics, vol. XXII, No. 10, 457–462, 463–466, 1969.
Rhodes et al., Nature, vol. 192, Dec. 9, 1961.

Primary Examiner—Jane T. Fan
Attorney, Agent, or Firm—Wolder, Gross & Yavner

[57] ABSTRACT

Antibiotic AM-3603 which is also designated as irumamycin is represented by the following formula:

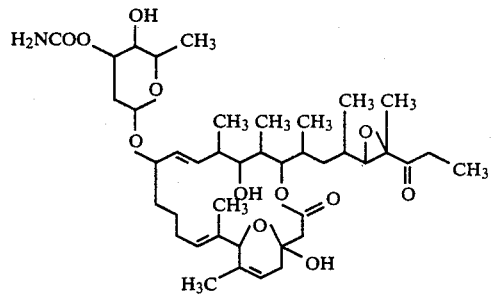

This substance is active upon certain Gram-positive bacteria, phytopathogenic fungi and dermatophytes, and is of interest in treating various diseases of humans and animals caused by infectious bacteria and fungi and also useful for agricultural purposes. Antibiotic AM-3603 may be prepared by fermentation, in which a microorganism capable of producing AM-3603 is cultured in a medium to accumulate AM-3603 in the cultured broths, from which AM-3603 is recovered. A preferred strain is Streptomyces sp. AM-3603 (FERM-P 5619; NRRL 12518).

7 Claims, 4 Drawing Figures

ANTIBIOTIC AM-3603

RELATED APPLICATION

This application is a continuation-in-part of Ser. No. 289,695 filed Sept. 2, 1981 now abandoned.

SUMMARY OF THE INVENTION

This invention relates to a new antibiotic designated by us as AM-3603, a process for producing the same and pharmaceutical composition containing the same. This invention is based upon the discovery that a certain microorganism which we have isolated from the soil of Iruma-shi, Saitama-ken, Japan, is capable of producing a new substance having antibiotic activity.

Thus, an object of this invention is to provide a new antibiotic designated by us as AM-3603, which is also designated by us as irumamycin.

The new antibiotic AM-3603 is stable in the form of whitish amorphous powder in its substantially pure form and possesses the following physico-chemical characteristics:

(1) Nature: neutral, lipophylic
(2) Melting point: 95°–97° C.
(3) Specific rotation: $[\alpha]_D^{26.5} = +9°$ (c=1, ethanol)
(4) Elemental analysis: C: 65.7%, H: 8.56%, N: 1.95%
(5) Molecular formula: $C_{41}H_{65}NO_{12}$
(6) Molecular weight: 763, FD-Mass m/z 745 ($M^+ - 18$)
(7) Chromatographic mobility: Chromatography using silica gel thin layer (0.2 mm) on aluminium plate [Kieselgel G, Art. 5554, commericially available from E. Merck AG., West Germany] carried out in conventional manner gave the following results.

| Solvent system | Rf |
| --- | --- |
| Benzene/acetone (1:1) | 0.56 |
| Chloroform/methanol (9:1) | 0.59 |
| Ethanol/water (2:1) | 0.74 |
| Ethyl acetate/pyridine/water (1:1:4) | 0.48 |
| Benzene/ethyl acetate (1:1) | 0.18 |

Figure 1:
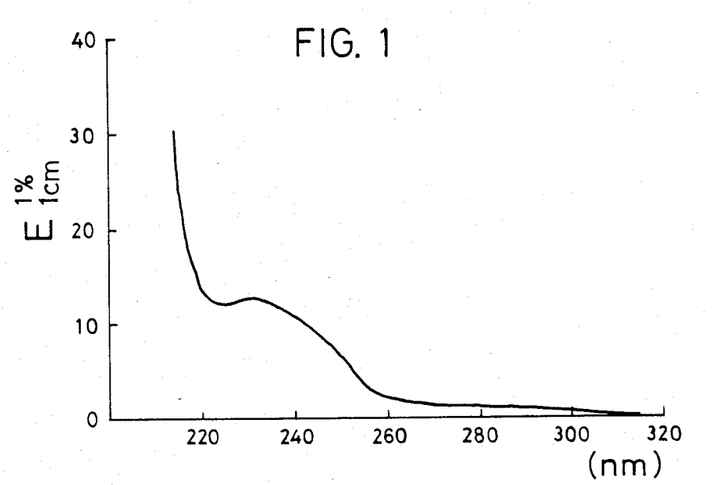
FIGS. 1 and 2 show respectively the ultraviolet and infrared absorption spectra of AM-3603 of the present invention.
Figure 2:
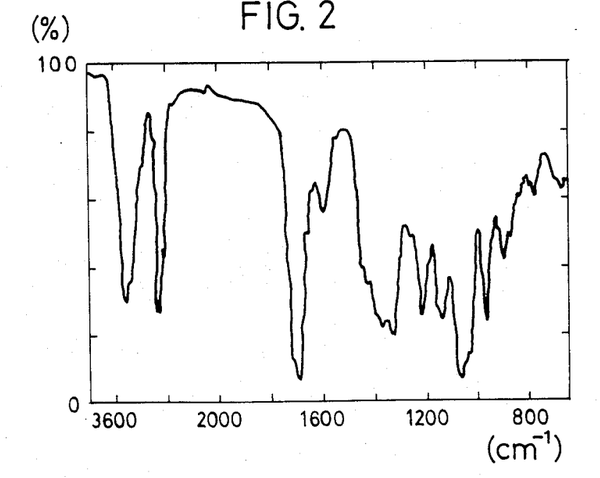
Figure 3:
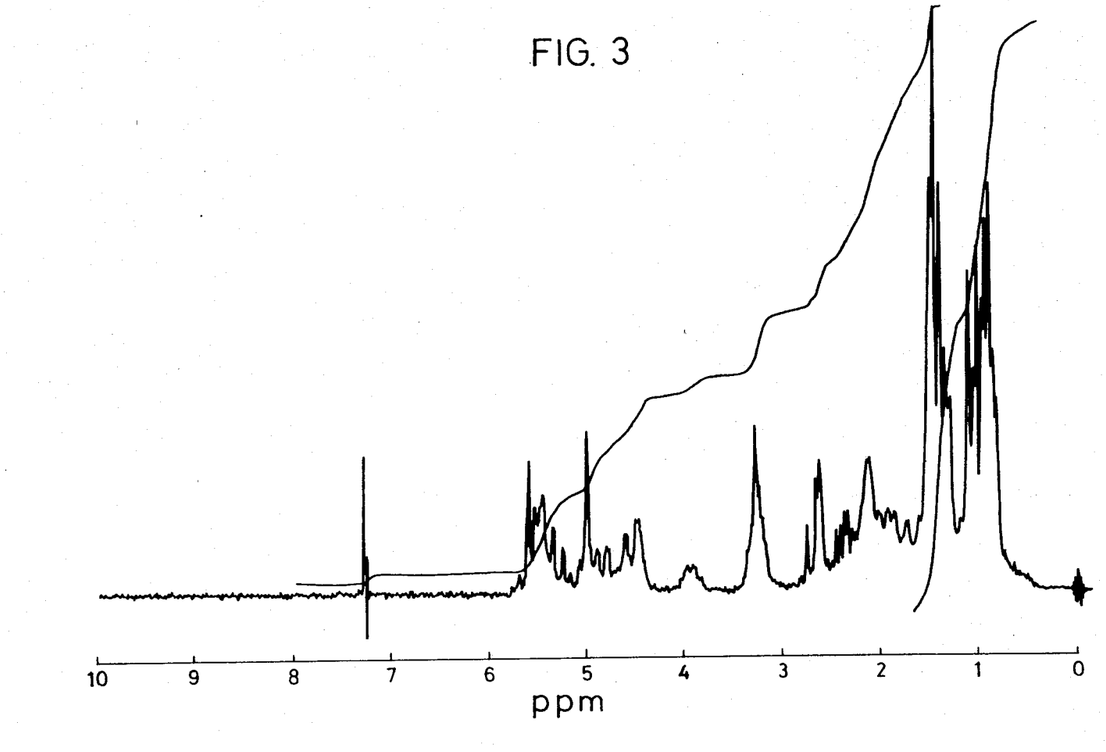
FIGS. 3 and 4 show respectively the $^1H$- and $^{13}C$-nuclear magnetic resonance spectra of the same.
Figure 4:
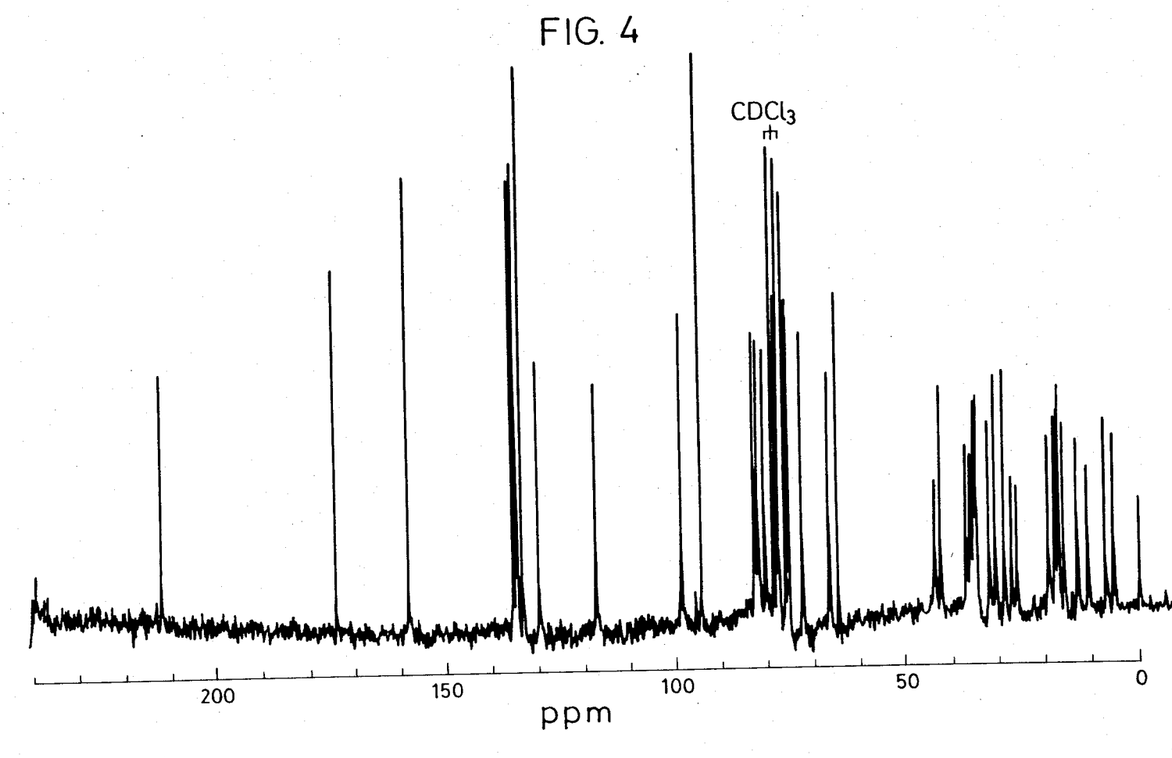

(8) Ultraviolet absorption spectrum: As shown in FIG. 1 (in ethanol)
(9) Infrared absorption spectrum: As shown in FIG. 2 (by KBr method)
(10) $^1$H-nmr spectrum: As shown in FIG. 3 (in $CDCl_3$)
(11) $^{13}$C-nmr spectrum: As shown in FIG. 4 (in $CDCl_3$)
(12) Solubility in various solvents: Soluble in methanol, ethanol, acetone, ethyl acetate, pyridine, diethyl ether, chloroform, carbon tetrachloride, benzene, toluene, dimethyl sulfoxide, cyclohexane etc. Insoluble in petroleum ether, n-hexane and water.
(13) Color reaction: Positive to anisaldehyde-sulfuric acid reaction, reactions with 2,4-dinitrophenylhydrazine, hydroxylamine, cerium sulfate and Dragendorff's reagent. Negative to Rydon-Smith reaction, ninhydrin reaction and reaction with ferric chloride.

From these characteristics it has been found that the new antibiotic AM-3603 is represented by the following formula (I):

BIOLOGICAL CHARACTERISTICS OF AM-3603

The results shown in the following Table 1 were obtained by using a sample of the active substance AM-3603 prepared in a similar manner to that hereinafter described Example 1. In this table, on each occasion, the MIC value for bacterium was determined by using a heart infusion agar medium (pH 7.0) after incubating at 37° C. for 20 hours, and the MIC value for fungus was determined by using a glucose potato agar medium (pH 6.8) after incubating at 27° C. for 44 hours. From Table 1, it is apparent that AM-3603 of this invention exhibits strong activity against minor Gram-positive bacteria and various phytopathogenic fungi and dermatophytes.

The acute toxicity [$LD_{50}$ in mice (ip.)] of AM-3603 is more than 200 mg/kg when determined by Behrens-Kärber method using male mice of ddy strain. It has also been found that AM-3603 is liable to induce deformation of certain fungi. Thus, AM-3603 is of interest in the treatment of various diseases of humans and animals caused by the infection of bacteria and fungi, and moreover this substance is expected to be useful for agricultural purposes.

For identifying purpose, the physico-chemical characteristics of AM-3603 have been compared with the corresponding characteristics of certain known antibiotics such as, for example, venturicidin [Rhodes et al: Nature, 192, 952–954 (1961)], aabomycin A [Misato et al: J. of Antibiotics, 22, 457–462 and 463–466 (1969)] and aabomycin S [Japanese Patent Publication No. 22119/75], as shown in Table 3, and the anti-phytopathogenic activity of AM-3603 has been compared with the corresponding activity of these known antibiotics in Table 2. From these tables, it is apparent that AM-3603 is a new substance.

The following Table 2 indicates the comparison of the anti-phytopathogenic activity of AM-3603 of this invention with those of certain known antibiotics, from which it is apparent that AM-3603 exhibits an excellent anti-phytopathogenic activity against certain microorganism.

TABLE 1

| Test organism | Minimum Inhibitory Concentration (μg/ml) MIC |
| --- | --- |
| Staphylococcus aureus FDA 209P | 100 |
| Bacillus subtilis PCI 219 | >100 |
| Sarcina lutea PCI 1001 | >100 |
| Mycobacterium smegmatis ATCC 607 | 100 |
| Corynebacterium paurometabolum KB-21 | 0.2 |
| Streptococcus pyogenes C 203 | 25 |
| Escherichia coli NIHJ | >100 |
| Klebsiella pneumoniae PCI 602 | >100 |
| Proteus vulgaris IFO 3167 | >100 |
| Pseudomonas aeruginosa P-3 | >100 |
| Candida albicans KF-1 | >100 |

TABLE 1-continued

| Minimum Inhibitory Concentration (μg/ml) | |
|---|---|
| Test organism | MIC |
| Sacchromyces sake KF-26 | >100 |
| Cryptococcus neoformans KF-33 | >100 |
| Penicillium crysogenum KF-97 | 0.2 |
| Aspergillus niger KF-102 | 25 |
| Aspergillus brevipus KF-201 | 1.56 |
| Sclerotinia cinerea KF-181 | <0.1 |
| Piricularia oryzae KF-180 | <0.1 |
| Alteraria kikuchiana KF-185 | 3.1 |
| Botrytis cinerea KF-184 | 12.5 |
| Trichophyton interdigitale KF-62 | 3.1 |
| Microsporum gypseum KF-65 | 50 |
| Mucor racemosus KF-223 | >100 |
| Fusarium oxysporum KF-166 | >100 |
| Pellicularia sasakii KF-219 | 25 |

TABLE 2

Comparison of anti-phytopathogenic activity of AM-3603 with other antibiotics

| Organism | | AM-3603 | Venturicidin | Botrycidin | Aabomycin A | Blasticidin S | Prumycin |
|---|---|---|---|---|---|---|---|
| | | | MIC (μg/ml)** | | | | |
| Piricularia oryzae | A* | 0.05 | <0.03 | 0.05 | <0.2 | >100 | >100 |
| | B | <0.03 | <0.03 | 0.03 | <0.2 | 25 | 100 |
| Sclerotinia cinerea | A | 0.05 | 0.78 | 0.4 | 0.2 | 50 | 1.56 |
| | B | 0.1 | 0.78 | 0.78 | 0.2 | 25 | 6.25 |
| Pellicularia sasakii | A | 0.4 | 1.56 | 12.5 | >100 | >100 | >100 |
| | B | 25 | >25 | >25 | >100 | >100 | >100 |
| Botrytis cinerea | A | — | — | — | >100 | 50 | 100 |
| | B | 6.25 | >25 | 12.5 | >100 | 100 | 50 |
| Alternaria kikuchiana | A | 50 | — | — | >100 | 50 | >100 |
| | B | 12.5 | >25 | 12.5 | 100 | 12.5 | 50 |

*A, isolate from infected plant;
B, laboratory stock culture
**Glucose-potato agar, 2-3 days
—, not tested

TABLE 3

| Comparison of AM-3603 with venturicidin, aabomycin A and aabomycin S | | | | |
|---|---|---|---|---|
| | AM-3603 | Venturicidin | Aabomycin A | Aabomycin S |
| Nature | neutral | neutral | weakly acidic | neutral |
| MP (°C.) | 95–97 | 142–143 | 144–145 | 98–99 |
| Mol. formula | $C_{41}H_{65}NO_{12}$ | $C_{43}H_{71}NO_{12}$ | $C_{39-40}H_{65-67}NO_{11}$ | $C_{36}H_{59}NO_{10}$ |
| Mol. wt. | 763 | 797 | 770 | 666 |
| $[\alpha]_D$ | +9° (c 1, EtOH) | +114° (c 1, CHCl$_3$) | +93.5° (c 1, CHCl$_3$) | +68° (c 1, MeOH) |
| Freely soluble in | MeOH, benzene, CCl$_4$ | MeOH | MeOH | MeOH |
| Slightly soluble in | | CCl$_4$ | benzene, CCl$_4$ | benzene, CCl$_4$ |
| Not soluble in | n-hexane, water | n-hexane, water | n-hexane, water | n-hexane, water |
| Color reaction | brown to black to H$_2$SO$_4$ on charring | | characteristic violet to H$_2$SO$_4$ on charring | characteristic violet to H$_2$SO$_4$ on charring |

According to another feature of this invention, we provide a process for producing an antibiotic AM-3603 as hereinbefore defined, in which a microorganism belonging to the genus Streptomyces and capable of producing AM-3603 is aerobically cultured in a medium to accumlate AM-3603 in the cultured broths and AM-3603 is recovered therefrom.

Preferred strains which may be used for the process of the invention are exemplified by Streptomyces sp. AM-3603 (FERM-P No. 5619; NRRL 12518) isolated by us from the soil of Iruma-shi, Saitama-ken, Japan.

Microbial charactertistics of the strain Streptomyces sp. AM-3603 (FERM-P 5619;NRRL 12518)

(1) Morphological characrerisitcs:

Vegetative hyphae develope well on both organic and synthetic madia, but usually have no septum. Aerial mycelia are abundantly formed on various media such as, for example, starch-inorganic salt agar medium, glucose-asparagine-agar medium, glycerol-asparagine-agar medium and the like, but are hardly formed on glycerol-calcium malate-agar medium, peptone-yeast-iron-agar medium, glucose-nitrate-agar medium and the like. Aerial mycelium is colored in white to pale yellow and shows a velvety or cottony appearance. When observed microscopically, sporophore is straight or loopy. Chains of more than 10 spores are formed. Spore surface is smooth. Sclerotium, sporangium and zoospore are not found.

(2) Cultural characteristics on various media:

The following Table 4 shows the results obtained by the method by E. B. Shering et al [Int. J. Syst. Bacteriol., Vol. 16, page 313 (1966)]. On each occasion, the color name and hue number (in the parenthesis) indicated in this table are expressed by referring to Color Harmony Manual [The 4th edition by Container Corpn. of America, Chicago, U.S.A.] and were determined after culturing at 27° C. for 2 weeks. The term "ISP" denotes the medium selected by the International Streptomyces Project.

TABLE 4

| Cultural characteristics of strain AM-3603 | |
|---|---|
| Medium | Cultural characteristics |
| Glucose-nitrate agar | G: moderate, flat, light ivory (2ca) |
| | R: light ivory (2ca) |
| | AM: none |
| | SP: none |
| Sucrose-nitrate agar | G: good, flat, light wheat (2ea) |
| | R: light wheat (2ea) |
| | AM: moderate, velvety, white (a) |

TABLE 4-continued

Cultural characteristics of strain AM-3603

| Medium | Cultural characteristics |
|---|---|
| Glycerol-calcium malate agar | SP: none<br>G: good, flat, colonial yellow (2ga)<br>R: colonial yellow (2ga)<br>AM: poor, cottony, light ivory (2ca) |
| Glucose-asparagine agar | Sp: none<br>G: good, raised, honey gold (2ic)<br>R: honey gold (2ic)<br>AM: abundant, cottony, white (a) |
| Glycerol-asparagine agar (ISP) | SP: none<br>G: good, raised, colonial yellow (2ga)<br>R: honey gold (2ic)<br>AM: abundant, velvety and cottony, light ivory (2ca) |
| Inorganic salts-starch agar (ISP) | SP: none<br>G: good, wrinkled, honey gold (2ic)<br>R: colonial yellow (2ga)<br>AM: abundant, cottony, white (a) |
| Tyrosine agar (ISP) | SP: none<br>G: good, raised, wrinkled, honey gold (2ic)<br>R: honey gold (2ic)<br>AM: abundant, velvety, light ivory (2ca) |
| Yeast extract-malt extract agar (ISP) | SP: none<br>G: good, wrinkled, honey gold (2ic)<br>R: honey gold (2ic)<br>AM: moderate, velvety, white (a) |
| Oatmeal agar (ISP) | SP: none<br>G: good, raised, squash yellow (2ia)<br>R: cream (1½ca)<br>AM: moderate, cottony, white (a) |
| Peptone-yeast extract iron agar (ISP) | SP: none<br>G: good, wrinkled, light wheat (2ea)<br>R: Bamboo (2gc)<br>AM: none |
| Glucose-peptone agar | SP: none<br>G: good, wrinkled, brite gold (2pc)<br>R: brite gold (2pc)<br>AM: poor, velvety, light ivory (2ia) |
| Peptone-beef extract agar | SP: none<br>G: good, flat, light wheat (2ea)<br>R: light wheat (2ea)<br>AM: none<br>SP: none |

Abbreviations:
G (Growth),
R (Reverse),
AM (Aerial mycelium),
SP (Soluble pigment) and
ISP (Medium employed by International Streptomyces Project).

(3) Physiological characteristics:

| | |
|---|---|
| (a) Formation of melanoid pigment:<br>    Tyrosine-agar medium<br>    Peptone-yeast extract-iron-agar medium<br>    Glucose-peptone-gelatin medium (stab culture at 21-23° C.)<br>    Tryptone-yeast extract broth | —<br>—<br>—<br>— |
| (b) Tyrosinase reaction | — |
| (c) Formation of hydrogen sulfide | — |
| (d) Reduction of nitrate | + |
| (e) Liquefaction of gelatin (glucose-peptone-gelatin medium) | + |
| (f) Hydrogenation of starch | + |
| (g) Coagulation of skim milk (37° C.) | — |
| (h) Peptonization of skim milk (37° C.) | + |
| (i) Decomposition of cellulose | — |
| (j) Growth temperature range 22 to 42° C. | |
| (k) Assimilability of various carbon sources (Pridham-Gottlieb madium)<br>    Assimilable: D-glucose, D-fructose, D-xylose, D-mannitol, L-inositol and raffinose.<br>    More or less assimilable:<br>      Salicin<br>    Not assimilable:<br>      L-arabinose, sucrose and L-rahmnose | |

(4) Cell wall composition:

Diaminopimelic acid is LL-isomer. Arabinose and galactose are not detected.

(5) Summary of microbiological characteristics of AM-3603:

The cell wall composition contains LL-diamonopimelic acid. Sporophore is straight, flexious or loopy and spore surface is smooth.

With respect to the cultural characteristics, vegitative hypha is yellowish and its color does not change in accordance with the change of pH. Aerial mycellium is whitish to yellowish. No soluble pigment and melanoid pigment are formed. From the results set forth, it is believed that this strain belongs to the genus Streptomyces and may be classified into the white or yellow series according to the classification by Pridham and Tresner[Bergy's Manual of Determinative Bactriology, 8th edition, pages 748-829 (1974)]. Any of the mutant strain of the present strain and other strains of the genus Streptomyces may be used for the purpose of this invention so long as they are capable of producing AM-3603 by fermentation.

Any synthetic or organic medium may be used for culturing the strain of the present invention when it contains suitable amounts of carbon, nitrogen, inorganic substances and, if desired, various other nutrients required for fermentation of the microorganisms for the genus Streptomyces. Any and all carbon sources and nitrogen sources may be used for the process of this invention if they are assimilable by the strain used. By way of examples, it is preferred to use as the carbon source, glucose, fructose, maltose, mannit, xylose, galactose, ribose, starch and hydrolyzate thereof at a concentration of from 0.1 to 5% calculated as glucose. It is also possible to use various organic acids such as, for example, gluconic acid, pyruvic acid, lactic acid, acetic acid and the like; various amino acids such as, for example, glycine, glutamic acid, alanine and the like; various alcohols such as, for example, methanol, ethanol and the like; normal paraffin and other non-aromatic hydrocarbons; and various plant and animal oils and fats as the carbon source.

The nitrogen sources which may be used for the process of this invention are exemplified by ammonia and ammonium salts of various organic and inorganic acids such as, for example, chloric, phosphoric, sulfuric, nitric and acetic acids; nitrogen-containing organic materials such as, for example, urea, peptone, NZ-amine, meat extract, yeast extract, dried yeast, corn steep liquor, casein hydrolyzate, fish meal, soybean meal, defatted soybean and digested products thereof. It is also possible to use various amino acids such as, for example, glycine, glutamic acid and alanine as the nitrogen source.

As the inorganic substances, it is possible to use, if desired, for example, various phosphates, magnesium sulfate, sodium chloride and traceable amounts of heavy metals.

When an auxotrophic strain is cultured by using an organic medium which does not contain a suitable nutrient required for the growth of such a strain, it is necessary to supplement the medium with such a nutrient.

The fermentation may be effected under aerobic conditions of shaking and/or submerged culture. A large amount of AM-3603 may be accumulated concurrently in the medium and mycelia, for example, by culturing at a temperature of from 22° to 40° C. for 1 to 8 days. A pH of the medium of 5 to 8 is preferred. After completion of fermentation, the antibiotic AM-3603 may be recovered, for example, in the following manner.

The cultured broth is separated into a filtrate and a sediment by centrifugation. The filtrate is treated with active carbon or synthetic macromolecular substnces to adsorb the active substance of this invention. The active substance is then extracted by using a suitable solvent. On the other hand, the active substance may also be extracted from the sediment by using a suitable solvent such as, for example, ethyl acetace, n-butanol, aqueous acetone and the like. The extract thus-obtained is concentrated and dried to obtain a crude AM-3603. The crude powder is then purified in conventional manner used for purifying lipophlic substances, for example, by the combined use of silica gel chromatography and other concentration method, salting-out method and the like. The active fractions thus-obtained are combined, concentrated and dried to yield AM-3603 in the form of powders. The product may be assayed in conventional manner, for example, by a biological method using a microorganism which is sensitive to AM-3603 (e.g. *Piricularia oryzae, Aspergillus niger* and *Sclerotinia cinerea*).

For the purpose of administering the active substance of this invention to humans, animals or plants with good results, there is provided a pharmaceutical composition, which comprises as active ingredient an effective amount of AM-3603 of this invention as hereinbefore defined, in association with a pharmaceutical carrier or excipient.

For human and animal use, the composition may be any and all forms adapted to oral, rectal, parenteral, percutaneous intramucous administration and the like. Thus, for example, the composition may be solid or liquid for oral administration and may take the forms of powders, syrups, capsules, granules, emulsions, suspension, drops and the like. Such composition comprises carrier or excipient conventionnally used in the pharmaceutical art. Thus, for example, suitable tabletting excipients include lactose, potato and soluble starches and magnesium stearate and for parenteral administration, the carrier may be a sterile water, physiological solution of sodium chloride, polypropylene glycol, ethanol, almond oil and the like, which may be put in an ampule or may be added to the active substance before use.

The composition may, if desired, further comprise, for example, bonding agents, stabilizing agents, emulsifiers, suspending agents, dispersing agents, lubricants, antiseptic agents, fillers and the like conventionally used in the pharmaceutical art.

For practical purpose, the composition may be formulated, for example, as buccals, troches, eye drops, suppositories and the like for intramucous administration, solutions, oils, suspensions and the like for injection agents, inhalants, sprays and the like for inhalational administration and ointments, plasters, liniments, bathes, sprays and the like for external administration.

Advantageously, the composition may be formulated as dosage units, each unit being adapted to supply a fixed dose of active ingredient. Suitable dosage unit forms are, for example, tablets, coated tablets, ampules, capsules, suppositories and the like.

The amount of the active ingredient preferably contained in such dosage unit forms may, for example, be within a range of from about 4 to about 10 for oral administration, about 2–3 for subcutaneous administration, about 1.5–3 for intramuscular administration, about 2–4 for baccals and troches and about 5–10 for suppositories, calculated on the basis of the preferred amount for intravenous injection (e.g. 0.05–2 mg/kg).

The compositions are exemplified as follows.

| | | |
|---|---|---|
| (1) Parenteral injection: | | |
| AM-3603 | 0.01 | g |
| Propylene glycol | 1.0 | ml |
| Water | 1.0 | ml |
| packed and sealed in a 5 ml ampule under sterilized conditions. | | |
| (2) Parenteral injection: | | |
| AM-3603 | 0.025 | g |
| Sorbitol | 0.5 | g |
| Hydrogenated castor oil | 0.025 | g |
| Made up with water to | 5 | ml |
| packed and sealed in a 10 ml amuple under sterilized conditions. | | |
| (3) Troche: | | |
| White sugar | 1 | g |
| AM-3603 | 0.05 | g |
| Starch | 0.05 | g |
| (4) Suppository: | | |
| Polyethylene glycol 400 | 0.8 | g |
| Polyethylene glycol 1500 | 0.2 | g |
| AM-3603 | 0.2 | g |
| (5) Syrup: | | |
| CMC-NA | 0.2 | g |
| Simple syrup | 20 | g |
| Ethylparaffin | 0.04 | g |
| AM-3603 | 0.1 | g |
| (6) Ointment: | | |
| Purified lanoline | 5 | g |
| Yellow wax | 5 | g |
| White vaselin | 87 | g |
| AM-3603 | 3 | g |

The antibiotic AM-3603 may also be applied to the organic material to be treated for the control of fungi at a dosage sufficient to exert fungicidal action. Accordingly, compositions of this invention may be used for the protection of carbohydrates, proteins and fats. AM-3603 is particularly suited for the treating of living plants such as vegetables, ornamental plants and fruit-bearing trees. Some of these compositions are also effective when applied directly to the soil for treating plant fungi. Also they may be used to treat organic fibers and fabrics and various cellulosic materials such as leather and wood.

In application to plants, fungicidal control is obtained in most instances by applying the antibiotic AM-3603 at a single dosage from about 2–100 g/10 a: the optimum amount within this range being largely dependent upon the plants to be treated. In application directly to the soil for use as a systemic fungicide, in most instances, the dosage or rate is from about 5–450 g/10 a.

The optimum dosage may be determined in each instance by one of the means conventional in the art. It is of course determined by and dependent upon the method of application, and, in the case of application to vegetation, the state and condition of growth of the vegetation to be treated, and the climatic conditions. In some cases, a multiple dosage may be beneficial.

The fungicidal compositions of this invention may or may not contain additionally in sufficient amounts other kinds of natural and synthetic fungicides to potentiate the fungicidal action of the antibiotic of this invention in admixture with a carrier material or conditioning agents of the kind used and commonly referred to in the art as a fungicide adjuvant or modifier. The conventional fungicide adjuvants are inert solids, hydrocarbon liquid diluents and surface-active agents. They provide formulations adapted for ready and efficient application using conventional applicator equipment. The concentration of AM-3603 in the fungicidal composition may be convenient and may vary, with differing conditions known in the art.

Solid compositions are preferably in the form of powders. They are compounded to be homogeneous powders that may be either used as such, diluted with inert solids to form dusts, or suspended in a suitable liquid medium for spray application. The powders usually comprise antibiotic AM-3603 admixed with appropriate amounts of conditioning agent. Natural clays, either adsorptive such as attapulgite or relatively non-absorptive such as kaolin clays, diatomaceous earth, walnut shell flour, tobacco dust, synthetic fine silica, calcium silicate and other inert solid carriers of the kind conventionally employed in powder fungicidal compositions may be used. The antibiotic AM-3603, and other fungicide, if any, usually make up from about 10–90% of these powder compositions. For conversion of the powders to dusts, talc, pyrophyllite, tobacco dust, volcanic ash and other dense inert solids may be used.

Liquid compositions employing antibiotic AM-3603 and one or more of fungicidally active ingredients may be prepared by admixing them with a suitable liquid diluent medium. The active ingredient may be either in solution or in suspension in the liquid medium. Typical of the liquid media commonly employed as fungicide adjuvants are kerosene, xylene, alcohol, alkylated naphthalene, liquefied petroleum gas and glycols. The active ingredient makes up, for example, from 1 to 50% of the liquid compositions. Some of these compositions are designed to be used as such, and others to be extended with large quantities of water.

The surfactants may be of the anionic, cationic or nonionic type, and their preferred examples include sodium oleate, sulfonated petroleum oils, alkyl aryl sulfonates, sodium lauryl sulfate, polyethylene oxides, ligin sulfonates etc.

The present invention also provides a pure culture of Streptomyces sp AM-3603 (FERM-P 5619;NRRL 12518) as hereinbefore defined.

The following non-limiting examples illustrate the invention.

EXAMPLE 1

A loopful mycelia and spores of Streptomyces sp. AM-3603 (FERM-P 5619; NRRL 12518) were taken out from a slant culture and inoculated into 100 ml of a seed medium [glycerol (1.0%), glucose (0.1%), soybean meal (1.0%) and sodium chloride (0.3%); pH 7.0] in a 500 ml Sakaguchi flask for culturing with shaking at 27° C. for 2 days to obtain a seed culture, of which one liter was then transferred into a fermentation medium [70 liter; composed of glycerol (2%), glucose (0.4%), soybean meal (1.0%) and sodium chloride (0.3%); pH 7.0] in a 100 l jar fermentor for culturing at 27° C. for 3 days with aeration (50 l/minute) and agitation (200 r.p.m.). The cultured broth (65 l) was adjusted to pH 7.0 with sodium hydroxide and extracted twice with ethyl acetate (each 18 l). The ethyl acetate layer was collected and concentrated to 500 ml under reduced pressure. The resultant solution was washed twice with water (each 100 ml) and dried by using sodium sulfate (100 g). The dried solution was concentrated and then 10 volumes of n-hexane were added to the concentrated solution to give a crude powder of AM-3603 (25.4 g), of which 25 g were dissolved in ethyl acetate (50 ml). To this solution was added silica gel (50 g; Art 7734, commercially available from E. Merck AG., West Germany). Ethyl acetate was removed from the solution by evaporation under reduced pressure to give a residue. The residue was suspended in chloroform (100 ml) and transferred to a column (5.3×49 cm) packed with silica gel (Art 7734) in chloroform (1.5 l). Column chromatography was carried out by using the following solvent systems one afte another: Chloroform (2 l), chloroform/methanol (300:1,3 l), chloroform/methanol (100:1, 3 l), chloroform/methanol (50:1, 5 l), chloroform/methanol (20:1, 2 l) and chloroform/methanol (5:1, 2 l). The eluate was divided into fractions (each 15–20 ml). The active fractions (Nos. 354–803) were collected and combined, and the combined fractions were concentrated and dried under reduced pressure to give a powder (20 g) containing AM-3603, of which 19 g were dissolved in ethyl acetate (50 ml), and a silica gel powder (40 g; Art 7734) was added to the solution. After this, the solution ws concentrated and dried under reduced pressure to give a residue. The resultant residue was suspended in benzene (80 ml) and transferred to a column (5.3×39 cm) packed with silica gel (400 g; Art 7734) in benzene (1.2 l).

Column chromatography was carried out using the following solvent systems one after another: Benzene (2 l), benzene/acetone (10:1, 3.5 l), benzene/acetone (6:1, 3.5 l), benzene/acetone (3:1, 3 l) and benzene/acetone (1:1, 2 l). The eluate was divided into fractions (each 15–20 ml). The active fractions (Nos. 320–558) were collected and combined and the combined fractions were concentrated under reduced pressure. Ten volumes of n-hexane were added to the concentrated solution to give a powder (11 g) containing AM-3603. A fraction (3 g) of this powder was dissolved in benzene (10 ml) and the solution was transferred to a cartridge column (5.7×30 cm) packed with a high porous silica gel (particle size; 80 μ) and chromatographed by the use of a Water Associates high pressure liquid chromatography system [PrePAK/System 500, commericially available from Japan Waters Co., Tokyo]. A solvent system of benzene/acetone (4:1, 5 l) was used as an eluant and the eluate was divided into fractions (each 50 ml). An aliquot of each fraction was chromatographed on a silica gel thin layer (0.2 mm; Art 5554, commercially available from E. Merck AG., West Germany) using a solvent system of benzene/acetone (1:1). On each occasion, the thin layer was sprayed with sulfuric acid and was then heated to develope the color. All of the fractions showing single spot [Nos. 19–37] were collected and combined. The combined fractions were concentrated and dried under reduced pressure to yield an amorphous whitish powder of AM-3603 of this invention (1.45 g), of which physico-chemical characteristics are as hereinbefore defined.

EXAMPLE 2

A wettable powder composed of AM-3603 (20%), sodium lauryl sulfate (3%), sodium lignin sulfonate (7%) and kaolin clay (70%) inhibited the growth of gray mold, when dispersed in water and sprayed on cucumber folliage, as follows.

Uninfected cucumber plants were cultured for 18 days by using unglazed pots (9 cm in diameter). The wettable powder was dispersed in water to give a final concentration of AM-3603 of from 50 to 200 ppm. On each occasion, the foliage of the plant was sprayed with the said suspension at a rate of 5 ml per foliage, and the plant was then incubated for one day at 25° C. at a relative humidity of 80%. After this, the thus-treated plant was exposed to an aqueous suspension of spores and mycelia of gray mold (*Botrytis cinerea*). Then the plant was incubated for one day at 25° C. and a relative humidity of 95%. Subsequently, the incubation was continued at 25° C. and a relative humidity of 75-80% for 10 days. The growth of the fungus was remarkably inhibited by treating with AM-3603, as is apparent from the comparison with untreated cucumber plants indicated in the following Table 5. The suspension used for infection contained more than $10^7$/ml of the spores and mycelia.

EXAMPLE 3

An wettable powder composed of AM-3603 (20%), sodium alkylnaphthalene sulfonate (2%), methyl cellulose (1%) and diatomaceous earth (77%) was dispersed in water and sprayed on cucumber plants at a concentration of AM-3603 of 50-200 ppm. The infection of the plants was significantly inhibited in the following manner.

The folliage of uninfected cucumber plants were treated in a similar manner to that described in Example 2 except the use of *Colletotricum agenarium* instead of gray mold. A marked inhibition of fungal disease was observed, as shown in Table 5, on the folliage of the antibiotic treated cucumber plants.

EXAMPLE 4

The wettable powder of Example 2, when diluted with water and applied on rice plants at a concentration of 200 ppm, protected the plant against *Cochliobolus miyabianus*. Uninfected rice plants were cultured for 45 days in unglazed pots (each having a diameter of 20 cm) to grow up to 70-80 cm in height. The wettable powder of Example 2 was diluted with water to give a final AM-3603 concentration of 200 ppm, and sprayed onto the folliage of the plants at a rate of 50 ml/pot. 24 hours after this, on each occasion, the sheath received 4 drops of an aqueous suspension of the spores and mycelia of *Cochliobolus miyabianus*. Then the plants were incubated for 4 days at 28°-30° C. at a relative humidity of more than 95%. After this, the plants were incubated for 6 days at 28° C. and a relative humidity of 70%. As a result of the exposure to fungi for 10 days in total, a marked inhibition of the infected lesions was found on the treated rice plants when compared with those on untreated plants. The results are shown in the following Table 5.

TABLE 5

| Pathogen | Plant infected | AM-3603 challenged (ppm) | Protection value |
| --- | --- | --- | --- |
| Botrytis | Cucumber | 200 | 98 |
|  |  | 100 | 97 |
|  |  | 50 | 97 |
| Colletotricum | Cucumber | 200 | 100 |
|  |  | 100 | 99.6 |
|  |  | 50 | 92 |
| Cochliobolus | Rice plant | 200 | 92 |

EXAMPLE 5

The following dust composition was dusted on eggplants at a rate of 20 g of AM-3603 per 10 ares. Gray mold was significantly prevented.

Antibiotic AM-3603: 30 (%);
Prophylite: 70 (%).

EXAMPLE 6

A dust composition of AM-3603 (20%) and talc (80%) protected significantly against gray mold, when dusted on peer trees at a rate of 60 g of AM-3603 per 10 ares of the orchard.

EXAMPLE 7

The following aqueous suspension inhibited significantly the growth of fungi growing at humid places in house.

Antibiotic AM-3603: 30 (%);
Florigel (hydrated attaoulite): 2 (%);
Polyvinylalcohol: 3 (%);
Water: 65 (%).

The suspension was diluted with water for use at a convenient concentration. When the suspension was diluted with water at a concentration of from 0.1 to 0.5 parts to 100 parts of water and sprayed on the wall of a house or on the gutters of a bathroom, washroom, kitchen and the like, which are always exposed to humid air, a remarked antifungal effect was observed.

We claim:

1. A substance designated as AM-3603 having antibiotic activity represented by the following formula:

[Chemical structure diagram showing a complex molecule with H₂NCOO, OH, CH₃ groups and a macrocyclic ring structure]

2. A composition having antibiotic activity comprising an antibiotic effective amount of AM-3603 as defined in claim 1 in combination with a pharmaceutically acceptable carrier or excipient.

3. A composition for the control of fungi in plants comprising as an active agent a fungicidal effective amount of AM-3603 in combination with a fungicide adjuvant.

4. The composition of claim 3 wherein said fungicide adjuvant is selected from the group consisting of inert solids, hydrocarbon liquid diluents and surface active agents.

5. The composition of claim 2 applied to plants at a dosage of 2 to 100 grams of AM-3603 per 10 acres of plants.

6. The composition of claim 2 applied to soil as a systemic fungicide at a dosage of 5 to 450 grams of AM-3603 per 10 acres of soil.

7. The composition of claim 2 for animal use containing the following amount of AM-3603 calculated on the basis of preferred amount for intravenous injection of 0.05 to 2 mg/kg of body weight: 4 to 10 for oral administration; 2 to 3 for subcutaneous administration; 1.5 to 3 for intramuscular administration; 2 to 4 for baccals and troches and 5 to 10 for suppositories.

* * * * *